United States Patent [19]
Larson et al.

[11] Patent Number: 5,773,434
[45] Date of Patent: Jun. 30, 1998

[54] FACILITATION OF AMPA RECEPTOR-MEDIATED SYNAPTIC TRANSMISSION IN BRAIN AS A TREATMENT FOR SCHIZOPHRENIA

[75] Inventors: John Larson, Costa Mesa; Gary Lynch, Irvine, both of Calif.; Gary A. Rogers, 3056 Foothill Rd., Santa Barbara, Calif. 93105

[73] Assignees: Gary A. Rogers, Santa Barbara; The Regents of the University of California, Oakland, both of Calif.

[21] Appl. No.: 521,022

[22] Filed: Aug. 30, 1995

[51] Int. Cl.[6] ............................ A61K 31/55; A61K 31/54
[52] U.S. Cl. .................. 514/212; 514/223.2; 514/229.2; 514/249; 514/321; 514/322; 514/338; 514/354; 514/410; 514/411; 514/423
[58] Field of Search ............................. 514/229.2, 223.2, 514/212, 249, 321, 322, 338, 354, 410, 411, 423

[56] References Cited

U.S. PATENT DOCUMENTS

| | | |
|---|---|---|
| 5,145,845 | 9/1992 | Johnson et al. . |
| 5,164,404 | 11/1992 | Dahl et al. . |
| 5,252,584 | 10/1993 | Carling et al. . |
| 5,268,378 | 12/1993 | Baker et al. . |
| 5,348,962 | 9/1994 | Kulagowski et al. . |
| 5,376,748 | 12/1994 | Carling et al. . |
| 5,488,049 | 1/1996 | Costa et al. ................. 514/223.2 |

FOREIGN PATENT DOCUMENTS

| | | |
|---|---|---|
| 2 265 372 | 9/1993 | United Kingdom . |
| 2 266 888 | 11/1993 | United Kingdom . |
| WO 93/11115 | 6/1993 | WIPO . |
| WO 94/02475 | 2/1994 | WIPO . |
| WO 94/26747 | 11/1994 | WIPO . |

OTHER PUBLICATIONS

Hcaplus abstract, AN 1995:66274 (1994) Cordi, A.A. et al. Pirotte, et al., "New Pyridothiadiazines, Processes for their Preparation, and Pharmaceutical Compositions Containing Them," Chemical Abstract No. 290897z, 122(23):1042, Jun. 5, 1995.

*Primary Examiner*—Marianne M. Cintins
*Assistant Examiner*—M. Moezie
*Attorney, Agent, or Firm*—Townsend and Townsend and Crew LLP

[57] ABSTRACT

Psychotic symptoms are treated by the administration of drugs which amplify the ability of natural stimulators of AMPA receptors to enhance the mediation of excitatory synaptic response. What is previously known about the activity and effectiveness of these drugs is unrelated to the etiology of psychotic symptoms. The invention finds particular utility in the treatment of schizophrenia.

22 Claims, 2 Drawing Sheets

FACILITATION OF AMPA RECEPTOR-MEDIATED SYNAPTIC TRANSMISSION IN BRAIN AS A TREATMENT FOR SCHIZOPHRENIA

GOVERNMENT RIGHTS

This invention was made with Government support under Grant No. F49620-92-J-0307 awarded by the U.S. Air Force and Grant No. MH-51151 awarded by the National Institutes of Mental Health. The Government has certain rights in this invention.

BACKGROUND OF THE INVENTION

Schizophrenia is a chronic psychotic mental disorder characterized by both positive symptoms (delusions, hallucinations, and formal thought disorder) and negative symptoms (flattened affect and social withdrawal). The estimated prevalence of schizophrenia among humans is 0.2–2.0% worldwide.

Schizophrenia is typically treated with a class of drugs called antipsychotics or neuroleptics that have a common mode of action as antagonists of brain dopamine receptors. The effectiveness of neuroleptics as well as other findings have led to the currently held hypothesis of schizophrenia known as the "dopamine hypothesis." This hypothesis posits that hyperactivity in the dopaminergic projections from the midbrain to limbic and cortical structures is responsible for the clinical symptoms of the disorder. The hypothesis is also supported by the finding that amphetamines, which among other things enhance dopamine release, produce psychotic symptoms in humans and aberrant behaviors in animals.

Heretofore, there has been no known connection between psychotic symptoms and stimulators of AMPA receptors.

SUMMARY OF THE INVENTION

It has now been discovered that psychotic symptoms can be treated by enhancement of glutamatergic transmission. It is known that glutamate is released by input axons onto α-amino-3-hydroxy-5-methyl-isoxazole-4-propionic acid ("AMPA") receptors, and that this release mediates excitatory currents at many sites in the telencephalon. It is also known that certain drugs are effective in facilitating these currents. What is offered by the present invention is the discovery that these drugs are also beneficial in the treatment of schizophrenia. The present invention therefore resides in the treatment of schizophrenia by pharmacologically amplifying the natural stimulators of AMPA receptors to enhance the mediation by those receptors of excitatory synaptic response. Among the compounds used in the practice of this invention is a novel group of compounds displaying these properties.

The experimental findings which support this discovery and examples of the types of drugs which are effective in its implementation are described in the succeeding sections of this specification.

DETAILED DESCRIPTION OF THE INVENTION AND PREFERRED EMBODIMENTS

Compounds useful in the practice of this invention are generally those which amplify the activity of the natural stimulators of AMPA receptors in mediating excitatory synaptic response. Certain groups of these compounds fall within generic structural classes. One such class is defined by Formula I:

In this formula:
$R^1$ is either N or CH;
m is either 0 or 1;
$R^2$ is a either $(CR^8_2)_{n-m}$ or $C_{n-m}R^8_{2(n-m)-2}$, in which:
n is 4, 5, 6, or 7; and
the $R^8$'s in any single compound are either the same or different, each $R^8$ being either H or $C_1$–$C_6$ alkyl, or one $R^8$ being combined with either $R^3$ or $R^7$ to form a single bond bridging the no. 3' and either the no. 2 or the no. 6 ring vertices or a single divalent linking moiety linking the no. 3' and either the no. 2 or the no. 6 ring vertices, examples of single divalent linking moieties being $CH_2$, $CH_2$—$CH_2$, CH=CH, O, NH, N($C_1$–$C_6$ alkyl), N=CH, N=C($C_1$–$C_6$ alkyl), C(O), O—C(O), C(O)—O, CH(OH), NH—C(O), and N($C_1$–$C_6$ alkyl)—C(O);
$R^3$, when not combined with any $R^8$, is either H, $C_1$–$C_6$ alkyl, or $C_1$–$C_6$ alkoxy;
$R^4$ is either H, OH, or $C_1$–$C_6$ alkoxy, or is combined with $R^5$;
$R^5$ is either combined with $R^4$ or is H, OH, $C_1$–$C_6$ alkoxy, amino, mono($C_1$–$C_6$ alkyl)amino, di($C_1$–$C_6$ alkyl)amino, or $CH_2OR^9$, in which:
$R^9$ is H, $C_1$–$C_6$ alkyl, an aromatic carbocyclic moiety, an aromatic heterocyclic moiety, an aromatic carbocyclic alkyl moiety, an aromatic heterocyclic alkyl moiety, or any such moiety substituted with one or more members of the group $C_1$–$C_3$ alkyl, $C_1$–$C_3$ alkoxy, hydroxy, halo, amino, alkylamino, dialkylamino, and methylenedioxy;
$R^6$ is either H or $CH_2OR^9$;
$R^4$ and $R^5$ when combined form a member selected from the group consisting of in which:
$R^{10}$ is either O, NH or N($C_1$–$C_6$ alkyl);
$R^{11}$ is either O, NH or N($C_1$–$C_6$ alkyl);
$R^{12}$ is either H or $C_1$–$C_6$ alkyl, and when two or more $R^{12}$'s are present in a single compound, such $R^{12}$'s are the same or different;
p is 1, 2, or 3; and
q is 1 or 2; and
$R^7$, when not combined with any $R^8$, is either H, $C_1$–$C_6$ alkyl, or $C_1$–$C_6$ alkoxy.

Within the scope of Formula I, certain subclasses are preferred. One of these is the subclass in which $R^2$ is $(CHR^8)_{n-m}$ or $C_{n-m}HR^8{}_{2(n-m)-3}$, and $R^3$ is H, $C_1$–$C_6$ alkyl, or $C_1$–$C_6$ alkoxy. Another is the subclass in which $R^2$ is $(CHR^8)_{n-m}$ or $C_{n-m}HR^8{}_{2(n-m)-3}$, and one $R^8$ is combined with either $R^3$ or $R^7$ to form a single bond bridging the 2 and 3' ring vertices or a single divalent linking moiety linking the 2 and 3' ring vertices, with $CH_2$, $CH_2$—$CH_2$, $CH=CH$, O, NH, $N(C_1$–$C_6$ alkyl), $N=CH$, $N=C(C_1$–$C_6$ alkyl), $C(O)$, $O$—$C(O)$, $C(O)$—$O$, $CH(OH)$, $NH$—$C(O)$, or $N(C_1$–$C_6$ alkyl)—$C(O)$ as the linking moiety. A preferred subclass of $R^2$ is $CHR^8$—$CH_2$—$CH_2$—$CH_2$ and $CHR^8$—$CH_2$—$CH_2$—$CH_2$. A preferred subclass of linking moieties is $CH_2$, $CH_2$—$CH_2$, $CH=CH$, O, NH, $C(O)$, and $CH(OH)$. A further preferred subclass is $CH_2$, O, NH, $C(O)$, and $CH(OH)$.

When $R^4$ and $R^5$ are combined, a preferred subclass for $R^{12}$ is H and $CH_3$, and preferred groups representing the combination of $R^4$ and $R^5$ are In these groups, $R^{10}$ and $R^{11}$ are both preferably O, and p is 1 or 2. Still further preferred subclasses are those in which m is zero.

A further class of compounds useful in the practice of the invention are those of Formula II:

In Formula II:
$R^{21}$ is either H, halo or $CF_3$;
$R^{22}$ and $R^{23}$ either are both H or are combined to form a double bond bridging the 3 and 4 ring vertices;
$R^{24}$ is either H, $C_1$–$C_6$ alkyl, $C_5$–$C_7$ cycloalkyl, $C_5$–$C_7$ cycloalkenyl, Ph, $CH_2Ph$, $CH_2SCH_2Ph$, $CH_2X$, $CHX_2$, $CH_2SCH_2CF_3$, $CH_2SCH_2CH=CH_2$, or and $R^{25}$ is a member selected from the group consisting of H and $C_1$–$C_6$ alkyl.

Within the scope of Formula II, certain subclasses are preferred. One of these is the subclass in which $R^{21}$ is Cl or $CF_3$, with Cl preferred. Another is the subclass in which all X's are Cl. Still another is the subclass in which $R^{22}$ and $R^{23}$ are both H. A preferred subclass of $R^{24}$ is that which includes $CH_2Ph$, $CH_2SCH_2Ph$, and Of the terms used in the definitions of these formulas:
"Carbocyclic moiety" denotes a ring structure in which all ring vertices are carbon atoms. The term encompasses both single ring structures and fused ring structures. Examples of aromatic carbocyclic moieties are phenyl and naphthyl.

"Heterocyclic moiety" denotes a ring structure in which one or more ring vertices are atoms other than carbon atoms, the remainder being carbon atoms. Examples of non-carbon atoms are N, O, and S. The term encompasses both single ring structures and fused ring structures. Examples of aromatic heterocyclic moieties are pyridyl, pyrazinyl, pyrimidinyl, quinazolyl, isoquinazolyl, benzofuryl, isobenzofuryl, benzothiofuryl, indolyl, and indolizinyl.

"Alkyl," when not preceded by a carbon atom range, denotes lower alkyl, including both straight chain and branched-chain. Preferred are $C_1$–$C_6$ alkyl, with $C_1$–$C_4$ alkyl more preferred and $C_1$–$C_2$ alkyl the most preferred. Examples are methyl, ethyl, propyl, isopropyl, isobutyl and tert-butyl.

"Halo" denotes a halogen atom, preferably F, Cl, Br, or I, more preferably Cl or F, and most preferably Cl. In Formula II, "X" represents a halogen atom.

Also in Formula II, "Ph" denotes a phenyl group.

Novel compounds within the scope of Formula II are those in which $R^{24}$ is either $C_5$–$C_7$ cycloalkyl, $C_5$–$C_7$ cycloalkenyl or Ph. Preferred compounds of this group are those in which $R^{21}$ is halo, $R^{22}$ is H, $R^{23}$ is H, and $R^{25}$ is H. Preferred substituents for $R^{24}$ are cyclohexyl, cyclohexenyl, and phenyl.

Compounds 1 through 25 below are examples of compounds within the scope of Formula I:

25

Compounds 26 through 40 below are examples of compounds within the scope of Formula II. Of these, Compounds 38, 39 and 40 are examples of the novel compounds.

26
bendroflumethiazide

27
benzthiazide

28
buthiazide

29
chlorothiazide

30
cyclothiazide

31
epithiazide 32
hydrochlorothiazide 33
hydroflumethiazide

34
methylclothiazide

35
methalthiazide 36
polythiazide 37
trichlormethiazide

38

39

39

The compounds described above can be prepared by conventional methods known to those skilled in the art of synthetic organic chemistry.

Certain compounds of Formula I, for example, can be prepared from an appropriately substituted benzoic acid by contacting the acid under conditions suitable to activate the carboxy group for the formation of an amide. This is accomplished, for example, by activating the acid with carbonyl diimidazole, or with a chlorinating agent such as thionyl chloride or oxalyl chloride to obtain the corresponding benzoyl chloride. The activated acid is then contacted with a nitrogen-containing heterocyclic compound under conditions suitable for producing the desired imide or amide. Alternatively, the substituted benzoic acid can be ionized by contact with at least two equivalents of base such as triethylamine in an inert solvent such as methylene chloride or alcohol-free chloroform, and the ionized benzoic acid can then be reacted with pivaloyl chloride or a reactive carboxylic acid anhydride such as trifluoroacetic anhydride or trichloroacetic anhydride, to produce a mixed anhydride. The mixed anhydride is then contacted with a nitrogen-containing heterocyclic compound to produce the desired imide or amide.

A further alternative to these methods, suitable for some of the compounds in Formula I, is to contact the appropriately selected 3,4-(alkylenedihetero)-benzaldehyde with ammonia to form an imine, then contacting the imine with benzoyloxycarbonyl chloride to form the benzoyloxycarbonyl imine. Suitable 3,4-(alkylenedihetero)-benzaldehydes include 3,4-(methylenedioxy)-benzaldehyde, 3,4-(ethylenedioxy)-benzaldehyde, 3,4-(propylenedioxy)-benzaldehyde, 3,4-(ethylidenedioxy)-benzaldehyde, 3,4-(propylenedithio)-benzaldehyde, 3,4-(ethylidenedithio)-benzaldehyde, 5-benzimidazolecarboxaldehyde, and 6-quinoxalinecarboxaldehyde. The benzoyloxycarbonyl imine is then contacted with a simple conjugated diene such as butadiene under cycloaddition reaction conditions, and then with a Lewis acid under conditions suitable for a Friedel-Crafts acylation. Examples of suitable conjugated dienes include butadiene, 1,3-pentadiene, and isoprene, and examples of suitable Lewis acids include $AlC_3$ and $ZnCl_2$.

Still further compounds within Formula I are prepared from 2,3-dihydroxy naphthalene. This starting material is reacted with 1,2-dibromoethane in the presence of base to produce an ethylenedioxy derivative of naphthalene, which is then reacted with an oxidizing agent such as potassium permanganate to produce 4,5-ethylenedioxyphthaldehydic acid. The latter is contacted with anhydrous ammonia to form an imine, which is then treated with a suitable carbonyl-activating agent such as dicyclohexylcarbodiimide under cyclization conditions to form an acyl imine. The acyl imine is then reacted with a simple conjugated diene to achieve cycloaddition.

Still further compounds within Formula I can be prepared by contacting an α-halotoluic acid with at least two equivalents of an alkali salt of a lower alcohol according to the Williamson ether synthesis to produce an ether linkage. The resulting alkoxymethylbenzoic acid is activated with carbonyldiimidazole, thionyl chloride, dicyclohexylcarbodiimide, or any other suitable activating agent, and reacted with a suitable amine to achieve a carboxamide linkage.

In an alternate to the scheme of the preceding paragraph, a formyl-substituted aromatic carboxamide is prepared by activation of an appropriate starting acid with a tertiary amine (for example, triethyl amine) plus an acid chloride (for example, pivaloyl chloride) to produce a mixed anhydride for coupling to a suitable amine. The formyl group is then reduced to an alcohol by a suitable reducing agent such as sodium borohydride. The alcohol is then converted to a leaving group which is replaceable by the alkali salt of an alcohol. The leaving group can be generated by reagents such as thionyl chloride, thionyl bromide, mineral acids such as hydrochloric, hydrobromic or hydroiodic acids, or the combined action of a tertiary amine plus either a suitable sulfonic anhydride or sulfonyl halide. Alternatively, the alcohol can be activated by removing the proton. This is achieved by the action of a strong base such as sodium hydride in an aprotic solvent such as dimethylformamide. The resulting alkoxide is then reacted with a suitable alkyl halide or other alkyl compound with a suitable leaving group to produce the desired ether linkage.

Fused ring structures such as those in which $R^3$ and one of the $R^8$'s of Formula I are combined to form a single linking group bridging the 2 and 3' carbon atoms can be synthesized in the following manner. The carboxyl group of an appropriately substituted salicylic acid is activated with carbonyldiimidazole in dichloromethane, chloroform, tetrahydrofuran, or other anhydrous solvent. An aminoalkylacetal such as $H_2N(CH_2)_3CH(OCH_2CH_3)_2$ is then added. The resulting amide is treated with an aryl or alkyl sulfonic acid, trifluoroacetic acid, or other strong acid, in a solvent of low basicity such as chloroform or dichloromethane, to cleave the acetal and cyclize the intermediate aldehyde with the amide nitrogen and the phenolic oxygen.

In all of these reaction schemes, the methods and reaction conditions for each of the individual reactions are well within the routine skill of, and will be readily apparent to, the synthesis chemist.

Compounds of Formula II and their methods of preparation are described in the literature. These methods are likewise within the routine skill of the synthesis chemist. The preparation of compounds such as bendroflumethiazide, for example, is described by Goldberg (Squibb), in U.S. Pat. No. 3,265,573 (1966). The preparation of compounds such as benzthiazide, epithiazide, methalthiazide and polythiazide is described by McManus (Pfizer), U.S. Pat. No. 3,009, 911 (1961). The preparation of buthiazide is described in U.K. Patent Nos. 861,367 and 885,078 (Ciba, 1961). The preparation of chlorothiazide is described by Hinkley (Merck & Co.), U.S. Pat. Nos. 2,809,194 (1957) and 2,937,169 (1960). The preparation of hydrochlorothiazide is described by Novello (Merck & Co.), U.S. Pat. No. 3,025,292 (1962); de Stevens and Werner (Ciba), U.S. Pat. No. 3,163,645 (1964); and Irons et al. (Merck & Co.), U.S. Pat. No. 3,164,588 (1965). The preparation of hydroflumethiazide is described by Lund et al. (Lovens), U.S. Pat. No. 3,254,076 (1966). The preparation of methylclothiazide is described by Close et al., *J. Am. Chem. Soc.* 82:1132 (1960). The preparation of trichlormethiazide is described by de Stevens et al., *Experientia* 16:113 (1960). The disclosures of each of these patents and papers is incorporated herein by reference.

The compounds of this invention can be incorporated into a variety of formulations for therapeutic administration. Examples are capsules, tablets, syrups, suppositories, and various injectable forms. Administration of the compounds can be achieved in various ways, including oral, bucal, rectal, parenteral, and intraperitoneal administration. Dose levels can vary widely, and optimal dosages for any particular patient or condition are readily determinable by those of skill in the art. Typical dosages can range from milligrams to decigrams. Preferred formulations of the compounds are oral preparations, particularly capsules or tablets containing each from about 1 milligram up to about 100 milligrams of active ingredient. Depending on the strength of the compound, a typical dosage may be one 10-mg tablet taken once a day, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release. Subjects contemplated for treatment in accordance with this invention include humans and laboratory animals.

EXAMPLE

Amphetamine-induced stereotypic behavior has been widely used as a model for human schizophrenia. The logic for this has been based primarily on two related sets of findings:

(1) Amphetamine abuse in humans is known to provoke psychotic symptoms including paranoid ideation, delusions, hallucinations, and stereotyped compulsive behaviors; and (2) Antipsychotic drugs that are effective in the treatment of human schizophrenia are also known to attenuate stereotypic behaviors induced in rats by amphetamines.

Finding no. (2) suggests that amphetamine-induced stereotypic behaviors in rats are a useful model for screening potential anti-schizophrenic drugs. Both findings have been instrumental in formulating the hypothesis that psychotic symptoms are due in part to hyperactive dopaminergic transmission since amphetamines enhance dopamine release and neuroleptic drugs are potent dopamine receptor antagonists.

The experiment described below used enhanced locomotion and stereotypic activity induced by amphetamines in rats as a model. Published authority for the use and reliability of this model is found in the following:

Janssen, P. A., et al., "Is it possible to predict the clinical effects of neuroleptic drugs (major tranquilizers) from animal data? IV. An improved experimental design for measuring the inhibitory effects of neuroleptic drugs on amphetamine- or apomorphine-induced 'Cheroing' and 'agitation' in rats," *Arzneimittel-Forschung* 17:841–854 (1967);

Bentall, A. C. C., et al., "Blockade of amphetamine-induced locomotor activity and stereotypy in rats by spiroperidol but not by an atypical neuroleptic, thioridazine," *Neuropharmacol.* 19:699–703 (1980);

Niemegeers, C. J. E., et al., "A systematic study of the pharmacological activities of dopamine antagonists," *Life Sci.* 24:2201–2216 (1979);

Hornykiewicz, O., "Psychopharmacological implications of dopamine and dopamine antagonists: a critical evaluation of current evidence," *Neurosci.* 3:773–783 (1978).

The experiment was performed as follows.

Male Sprague-Dawley rats aged 2 to 4 months were maintained on a 12:12 hour light:dark cycle with lights on at 7:00 a.m. For the tests, a clear PLEXIGLAS test cage (50 cm×25 cm×80 cm) in a partially darkened room with a small fan providing background noise was used. The rats were placed in the test cage for a fifteen-minute habituation period prior to receiving injections. Methamphetamine (MAMP; 2.0 mg/kg) was purchased from Research Biochemicals, Inc., R.B.I., Natick, Mass., USA) and was dissolved in physiological saline. The test drug, (R,S)-pyrazino[2,3-g]-2,3-dihydro-1H-pyrrolo[2,1-b] [1,3]benzoxazine-11(3aH)-one (compound no. 18 above), was dissolved in a 33% (weight/volume) 2-hydroxypropyl-$\beta$-cyclodextrin (R.B.I.) solution (50% physiological saline and 50% water). Each rat received an intraperitoneal injection of MAMP (2.0 mg/kg), MAMP (2.0 mg/kg) plus cyclodextrin vehicle, or MAMP (2.0 mg/kg) plus the test compound (15.0 mg/kg). The rats were then returned to the test cage and left undisturbed for two hours while their behaviors were videotaped continuously.

A trained observer, ignorant of the treatment conditions, viewed the videotapes and scored stereotypic rearing and locomotor behavior. The rearing was measured as the number of seconds spent rearing (both forelimbs lifted out of contact with the floor) per 30-second observation period at 5-minute intervals. Locomotor behavior was measured as the number of center-line crossings per 5-minute period. All observations were made on portions of the videotapes taken at fifteen-minute intervals within one hour after the injections. The results are presented in FIGS. 1 and 2, respectively, as averages (mean±s.e.m.) of these measures taken fifteen minutes apart.

Figure 1:
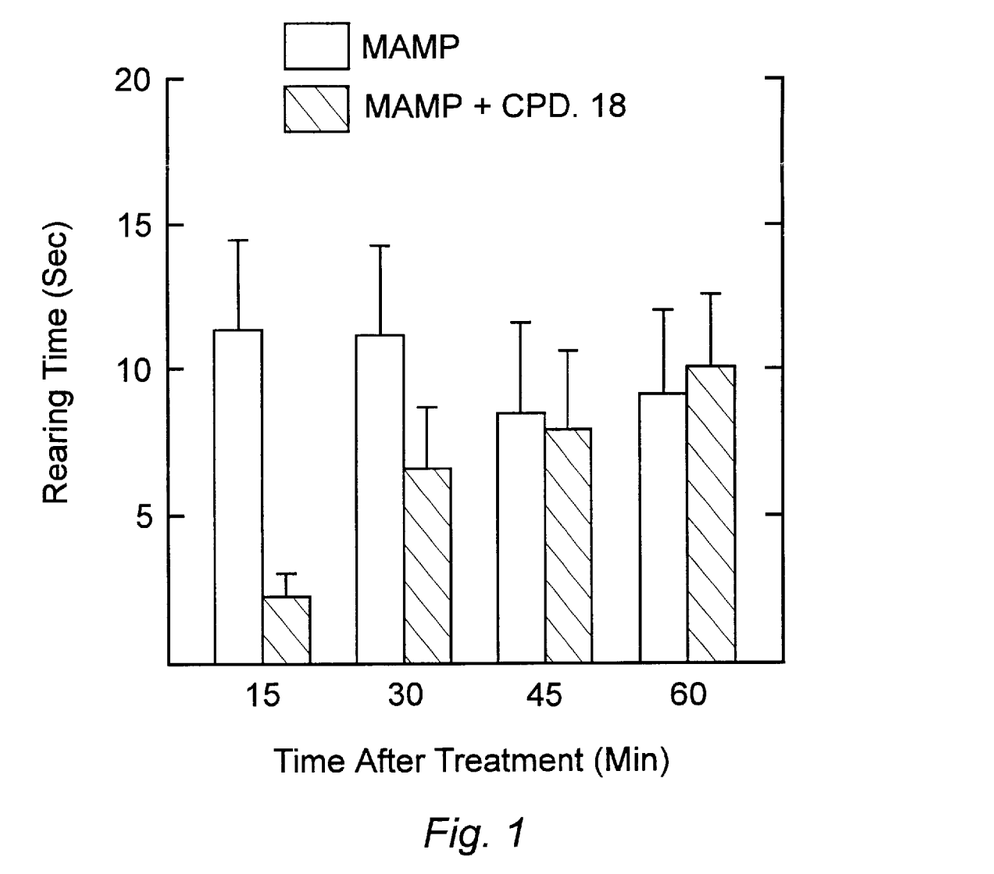
FIG. 1 is a bar graph showing the results of a rearing experiment in a rat model using a drug in accordance with the present invention.
Figure 2:
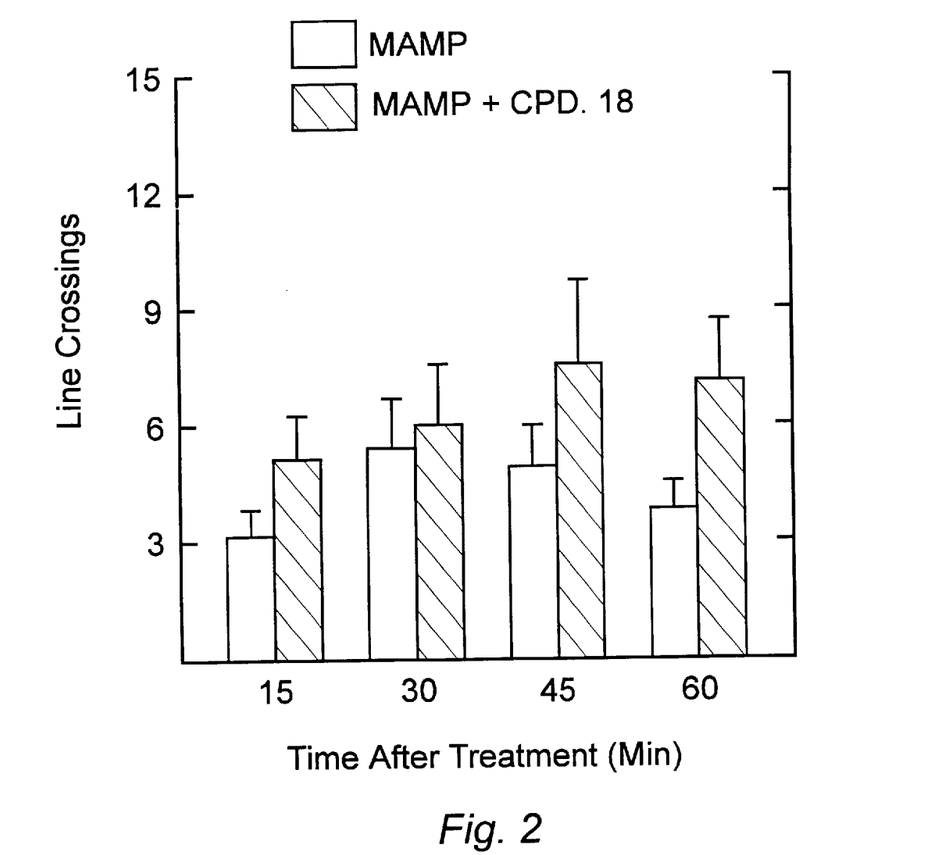
FIG. 2 is a bar graph showing the results of an exploratory activity test in a rat model, using the same drug used in FIG. 1.

Although not shown in the figures, no significant differences were observed in either of the two tests between animals receiving MAMP alone and those receiving MAMP plus cyclodextrin vehicle. The data for these two groups were therefore pooled.

FIG. 1 shows the average time spent rearing in 30-second sampling periods. The open bars represent the average of the pooled results of rats treated with MAMP alone and MAMP plus the vehicle, while the shaded bars represent the average of the results of rats treated with MAMP plus the test compound. Analysis of the variance indicated a significant treatment X time interaction ($F_{3,54}$=6.91, p<0.001), and post-hoc tests showed that rearing time was significantly reduced by the test compound during the first 15-minute period after the injections (p<0.01).

FIG. 2 shows the average number of center-line crossings made during the 5-minute sampling periods. Here again, the open bars represent the average of the pooled results of rats treated with MAMP alone and MAMP plus the vehicle, while the shaded bars represent the average of the results of rats treated with MAMP plus the test compound. There were no significant differences in results between groups given MAMP-alone and those given MAMP plus the test compound for this measure of exploratory activity (treatment X time $F_{3,54}$=0.70, p>0.5).

The test results indicate that facilitation of AMPA-type glutamate receptors can offset the stereotypic behavior (rearing) induced in rats by methamphetamine. Since there is little evidence that amphetamines directly interact with glutamatergic transmission, the results suggest that glutamatergic and dopaminergic inputs interact in neural systems that are involved in generating stereotypic behaviors and that these interactions are functionally antagonistic. Thus, induction of stereotypic activity by the enhanced dopamine release presumably caused by amphetamines can be counteracted by facilitation of AMPA receptors at glutamatergic synapses.

The foregoing is offered primarily for purposes of illustration. It will be readily apparent to those skilled in the art that the formulations, dosages, methods of administration, and other parameters of this invention may be further modified or substituted in various ways without departing from the spirit and scope of the invention.

We claim:

1. A method for treating schizophrenia in a subject, said method comprising pharmacologically amplifying natural stimulators of AMPA receptors in said subject to enhance the mediation by said receptors of excitatory synaptic response, said amplification being sufficient to reduce the symptoms of schizophrenia.

2. A method in accordance with claim 1 comprising pharmacologically amplifying said natural stimulators by administering to said subject an effective amount of a compound having the following formula, with ring vertices numbered as shown:

in which:
R$^1$ is a member selected from the group consisting of N and CH;
m is 0 or 1;
R$^2$ is a member selected from the group consisting of $(CR^8{}_2)_{n-m}$ and $C_{n-m}R^8{}_{2(n-m)-2}$, in which n is 4, 5, 6, or 7, the R$^8$'s in any single compound being the same or different, each R$^8$ being a member selected from the group consisting of H and C$_1$–C$_6$ alkyl, or one R$^8$ being combined with either R$^3$ or R$^7$ to form a single bond linking the no. 3' ring vertex to either the no. 2 or the no. 6 ring vertices or a single divalent linking moiety linking the no. 3' ring vertex to either the no. 2 or the no. 6 ring vertices, the linking moiety being a member selected from the group consisting of CH$_2$, CH$_2$—CH$_2$, CH=CH, O, NH, N(C$_1$–C$_6$ alkyl), N=CH, N=C (C$_1$–C$_6$ alkyl), C(O), O—C(O), C(O)—O, CH(OH), NH—C(O), and N(C$_1$–C$_6$ alkyl)—C(O);
R$^3$, when not combined with any R$^8$, is a member selected from the group consisting of H, C$_1$–C$_6$ alkyl, and C$_1$–C$_6$ alkoxy;
R$^4$ is either combined with R$^5$ or is a member selected from the group consisting of H, OH, and C$_1$–C$_6$ alkoxy;
R$^5$ is either combined with R$^4$ or is a member selected from the group consisting of H, OH, C$_1$–C$_6$ alkoxy, amino, mono(C$_1$–C$_6$ alkyl)amino, di(C$_1$–C$_6$ alkyl) amino, and CH$_2$OR$^9$, in which R$^9$ is a member selected from the group consisting of H, C$_1$–C$_6$ alkyl, an aromatic carbocyclic moiety, an aromatic heterocyclic moiety, an aromatic carbocyclic alkyl moiety, an aromatic heterocyclic alkyl moiety, and any such moiety substituted with one or more members selected from the group consisting of C$_1$–C$_3$ alkyl, C$_1$–C$_3$ alkoxy, hydroxy, halo, amino, alkylamino, dialkylamino, and methylenedioxy;
R$^6$ is either H or CH$_2$OR$^9$;
R$^4$ and R$^5$ when combined form a member selected from the group consisting of in which:
R$^{10}$ is a member selected from the group consisting of O, NH and N(C$_1$–C$_6$ alkyl);
R$^{11}$ is a member selected from the group consisting of O, NH and N(C$_1$–C$_6$ alkyl);
R$^{12}$ is a member selected from the group consisting of H and C$_1$–C$_6$ alkyl, and when two or more R$^{12}$'s are present in a single compound, such R$^{12}$'s are the same or different;
p is 1, 2, or 3; and
q is 1 or 2; and
R$^7$, when not combined with any R$^8$, is a member selected from the group consisting of H, C$_1$–C$_6$ alkyl, and C$_1$–C$_6$ alkoxy.

3. A method in accordance with claim 2 in which R$^2$ is a member selected from the group consisting of $(CHR^8)_{n-m}$ and $C_{n-m}HR^8{}_{2(n-m)-3}$, and R$^3$ is a member selected from the group consisting of H, C$_1$–C$_6$ alkyl, and C$_1$–C$_6$ alkoxy.

4. A method in accordance with claim 2 in which R$^2$ is a member selected from the group consisting of $(CHR^8)_{n-m}$ and $C_{n-m}HR^8{}_{2(n-m)-3}$, and one R$^8$ is combined with either R$^3$ or R$^7$ to form a single bond linking the no. 3' ring vertex to either the no. 2 or the no. 6 ring vertices or a single divalent linking moiety linking the no. 3' ring vertex to either the no. 2 or the no. 6 ring vertices, the linking moiety being a member selected from the group consisting of CH$_2$, CH$_2$—CH$_2$, CH=CH, O, NH, N(C$_1$–C$_6$ alkyl), N=CH, N=C (C$_1$–C$_6$ alkyl), C(O), O—C(O), C(O)—O, CH(OH), NH—C (O), and N(C$_1$–C$_6$ alkyl)—C(O).

5. A method in accordance with claim 2 in which R$^2$ is a member selected from the group consisting of $(CHR^8)_{n-m}$ and $C_{n-m}HR^8{}_{2(n-m)-3}$, and one R$^8$ is combined with either R$^3$ or R$^7$ to form a single bond linking the no. 3' ring vertex to either the no. 2 or the no. 6 ring vertices or a single divalent linking moiety linking the no. 3' ring vertex to either the no. 2 or the no. 6 ring vertices, the linking moiety being a member selected from the group consisting of CH$_2$, CH$_2$— CH$_2$, CH=CH, O, NH, C(O), and CH(OH).

6. A method in accordance with claim 2 in which R$^2$ is a member selected from the group consisting of $(CHR^8)_{n-m}$ and $C_{n-m}HR^8{}_{2(n-m)-3}$, and one R$^8$ is combined with either R$^3$ or R$^7$ to form a single divalent linking moiety linking the no. 3' ring vertex to either the no. 2 or the no. 6 ring vertices, the linking moiety being a member selected from the group consisting of CH$_2$, O, NH, C(O), and CH(OH).

7. A method in accordance with claim 2 in which m is zero, $R^2$ is a member selected from the group consisting of $CHR^8$—$CH_2$—$CH_2$—$CH_2$ and $CHR^8$—$CH_2$—$CH_2$—$CH_2$—$CH_2$, in which $R^8$ is combined with $R^7$ to form a single divalent linking moiety linking the 2 and 3' ring vertices, the linking moiety being a member selected from the group consisting of $CH_2$, O, NH, C(O), and CH(OH).

8. A method in accordance with claim 2 in which m is zero, $R^2$ is a member selected from the group consisting of $CHR^8$—$CH_2$—$CH_2$—$CH_2$ and $CHR^8$—$CH_2$—$CH_2$—$CH_2$—$CH_2$, in which $R^8$ is combined with $R^7$ to form a single divalent linking moiety linking the 2 and 3' ring vertices, the linking moiety being a member selected from the group consisting of $CH_2$, O, and NH.

9. A method in accordance with claim 2 in which $R^4$ and $R^5$ are combined to form a member selected from the group consisting of 10. A method in accordance with claim 9 in which $R^{12}$ is a member selected from the group consisting of H and $CH_3$.

11. A method in accordance with claim 2 in which $R^4$ and $R^5$ are combined to form a member selected from the group consisting of in which $R^{12}$ is a member selected from the group consisting of H and $CH_3$.

12. A method in accordance with claim 2 in which:

m is zero;

$R^2$ is a member selected from the group consisting of $CHR^8$—$CH_2$—$CH_2$—$CH_2$ and $CHR^8$—$CH_2$—$CH_2$—$CH_2$—$CH_2$, in which $R^8$ is combined with $R^7$ to form a single divalent linking moiety linking the 2 and 3' ring vertices, the linking moiety being a member selected from the group consisting of $CH_2$, O, NH, C(O), and CH(OH);

$R^4$ and $R^5$ are combined to form a member selected from the group consisting of $R^{10}$ is O;

$R^{11}$ is O;

$R^{12}$ is a member selected from the group consisting of H and $CH_3$.

13. A method in accordance with claim 2 in which $R^4$ and $R^5$ are combined to form a member selected from the group consisting of in which $R^{10}$ is O, $R^{11}$ is O, and $R^{12}$ is a member selected from the group consisting of H and $CH_3$.

14. A method in accordance with claim 2 in which: m is zero;

$R^2$ is a member selected from the group consisting of $CHR^8$—$CH_2$—$CH_2$—$CH_2$ and $CHR^8$—$CH_2$—$CH_2$—$CH_2$—$CH_2$, in which $R^8$ is combined with $R^7$ to form a single divalent linking moiety linking the 2 and 3' ring vertices, the linking moiety being a member selected from the group consisting of $CH_2$, O, and NH;

$R^4$ and $R^5$ are combined to form a member selected from the group consisting of $R^{10}$ is O;

$R^{11}$ is O; and $R^{12}$ is a member selected from the group consisting of H and $CH_3$.

15. A method in accordance with claim 2 in which:

m is zero;

$R^1$ is N;

$R^2$ is $CHR^8$—$CH_2$—$CH_2$—$CH_2$;

$R^3$ is H;

$R^3$ is H;

$R^4$ and $R^5$ are combined to form $R^6$ is H;

$R^8$ is combined with $R^7$ to form a single O atom linking the 2 and 3' ring vertices; and $R^{12}$ is H.

16. A method in accordance with claim 1 comprising pharmacologically amplifying said natural stimulators by administering to said subject an effective amount of a compound having the following formula, with ring vertices numbered as shown:

in which:

R²¹ is a member selected from the group consisting of H, halo and CF₃;

R²² and R²³ either are both H or are combined to form a double bond bridging the 3 and 4 ring vertices;

R²⁴ is a member selected from the group consisting of H, $C_1$–$C_6$ alkyl, $C_5$–$C_7$ cycloalkyl, $C_5$–$C_7$ cycloalkenyl, Ph, $CH_2Ph$, $CH_2SCH_2Ph$, $CH_2X$, $CHX_2$, $CH_2SCH_2CF_3$, $CH_2SCH_2CH{=}CH_2$, and where Ph is phenyl and X is halo; and R²⁵ is a member selected from the group consisting of H and $C_1$–$C_6$ alkyl.

17. A method in accordance with claim 16 in which:

R²¹ is a member selected from the group consisting of Cl and CF₃;

R²² and R²³ either are both H or are combined to form a double bond bridging the 3 and 4 ring vertices;

R²⁴ is a member selected from the group consisting of H, $CH_2CH(CH_3)_2$, cyclohexyl, cyclohexenyl, Ph, $CH_2Ph$, $CH_2SCH_2Ph$, $CH_2Cl$, $CHCl_2$, $CH_2SCH_2CF_3$, $CH_2SCH_2CH{=}CH_2$, and where Ph is phenyl; and

R²⁵ is a member selected from the group consisting of H and CH₃.

18. A method in accordance with claim 16 in which:

R²¹ is Cl;

R²² and R²³ are both H;

R²⁴ is a member selected from the group consisting of cyclohexyl, cyclohexenyl, Ph, CH₂Ph, CH₂SCH₂Ph, and where Ph is phenyl; and

R²⁵ is H.

19. A method in accordance with claim 16 in which said compound is

20. A method in accordance with claim 16 in which said compound is

21. A method in accordance with claim 16 in which said compound is

22. A method in accordance with claim 16 in which said compound is

* * * * *

UNITED STATES PATENT AND TRADEMARK OFFICE
CERTIFICATE OF CORRECTION

PATENT NO. : 5,773,434
DATED : June 30, 1998
INVENTOR(S) : John LARSON et al.

It is certified that error appears in the above-identified patent and that said Letters Patent is hereby corrected as shown below:

In column 15, claim 9 in the structural formula, approximately at line 24, in the compound on the left side, change the single N bond to a double bond.

In column 15, claim 12, in the structural formula, approximately at line 60, in the compound on the left side, delete "$(C_l R^{12}_{2q-1})$" and insert therefor --$(C_q R^{12}_{2q-1})$--.

In column 16, claim 14, in the structural formula, approximately at lines 30-33, in the compound on the left side, change the double $R^{11}$ bond to a single bond (as shown on the attached page); delete "$(CR^{12}_2)$" and insert therefor --$(CR^{12}_2)p$--.

In column 16, claim 15, approximately at line 47, delete "$R^3$ is H".

Signed and Sealed this

Tenth Day of November 1998

Attest:

BRUCE LEHMAN

*Attesting Officer*   *Commissioner of Patents and Trademarks*